(12) United States Patent
Takemoto

(10) Patent No.: US 11,331,089 B2
(45) Date of Patent: May 17, 2022

(54) OVERTUBE AND MEDICAL SYSTEM

(71) Applicant: OLYMPUS CORPORATION, Tokyo (JP)

(72) Inventor: Shotaro Takemoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 270 days.

(21) Appl. No.: 16/578,483

(22) Filed: Sep. 23, 2019

(65) Prior Publication Data

US 2020/0015797 A1 Jan. 16, 2020

Related U.S. Application Data

(63) Continuation of application No. PCT/JP2017/013983, filed on Apr. 3, 2017.

(51) Int. Cl.
*A61B 17/00* (2006.01)
(52) U.S. Cl.
CPC ............. *A61B 17/00234* (2013.01); *A61B 2017/0042* (2013.01); *A61B 2017/00292* (2013.01); *A61B 2017/00367* (2013.01); *A61B 2017/00469* (2013.01)
(58) Field of Classification Search
CPC .... A61B 17/00234; A61B 2017/00292; A61B 2017/00367; A61B 2017/0042; A61B 2017/00469
See application file for complete search history.

(56) References Cited

U.S. PATENT DOCUMENTS

| | | | |
|---|---|---|---|
| 6,783,491 B2 | 8/2004 | Saadat et al. |
| 6,790,173 B2 | 9/2004 | Saadat et al. |
| 6,837,847 B2 | 1/2005 | Ewers et al. |
| 6,942,613 B2 | 9/2005 | Ewers et al. |
| 6,960,162 B2 | 11/2005 | Saadat et al. |
| 6,960,163 B2 | 11/2005 | Ewers et al. |
| 7,041,052 B2 | 5/2006 | Saadat et al. |
| 7,128,708 B2 | 10/2006 | Saadat et al. |
| 7,704,264 B2 | 4/2010 | Ewers et al. |
| 7,744,613 B2 | 6/2010 | Ewers et al. |

(Continued)

FOREIGN PATENT DOCUMENTS

| | | |
|---|---|---|
| EP | 2248483 A1 | 11/2010 |
| JP | 2005-46273 A | 2/2005 |

(Continued)

OTHER PUBLICATIONS

International Search Report dated Jun. 20, 2017 issued in PCT/JP2017/013983.

*Primary Examiner* — Brooke Nicole Labranche
(74) *Attorney, Agent, or Firm* — Scully, Scott, Murphy & Presser, P.C.

(57) ABSTRACT

An overtube is provided with a flexible elongated portion provided with a channel, the channel is configured to pass therethrough in a longitudinal direction of the elongated portion so as to insert a medical device; a shape fixing mechanism provided in the elongated portion, and the shape fixing mechanism switches the state of the elongated portion between a bendable state and a shape-fixed state; and a gate mechanism disposed on a base-end side of the elongated portion, the gate mechanism is configured to close the channel when the state of the elongated portion is switched to the bendable state, and open the channel when the state of the elongated portion is switched to the shape-fixed state.

20 Claims, 10 Drawing Sheets

(56) References Cited

U.S. PATENT DOCUMENTS

| | | |
|---|---|---|
| 7,955,340 B2 | 6/2011 | Michlitsch et al. |
| 8,343,175 B2 | 1/2013 | Ewers et al. |
| 8,574,243 B2 | 11/2013 | Saadat et al. |
| 2003/0233025 A1 | 12/2003 | Saadat et al. |
| 2003/0233026 A1 | 12/2003 | Saadat et al. |
| 2003/0233027 A1 | 12/2003 | Ewers et al. |
| 2003/0233056 A1 | 12/2003 | Saadat et al. |
| 2003/0233057 A1 | 12/2003 | Saadat et al. |
| 2003/0233058 A1 | 12/2003 | Ewers et al. |
| 2003/0233066 A1 | 12/2003 | Ewers et al. |
| 2005/0075653 A1 | 4/2005 | Saadat et al. |
| 2005/0137454 A1 | 6/2005 | Saadat et al. |
| 2005/0137455 A1 | 6/2005 | Ewers et al. |
| 2006/0058582 A1 | 3/2006 | Maahs et al. |
| 2006/0111614 A1 | 5/2006 | Saadat et al. |
| 2010/0324370 A1 | 12/2010 | Dohi et al. |

FOREIGN PATENT DOCUMENTS

| | | |
|---|---|---|
| JP | 2009-279412 A | 12/2009 |
| JP | 2010-360 A | 1/2010 |
| JP | 2013-176418 A | 9/2013 |
| WO | WO 03/105563 A2 | 12/2003 |
| WO | WO 2009/107792 A1 | 9/2009 |

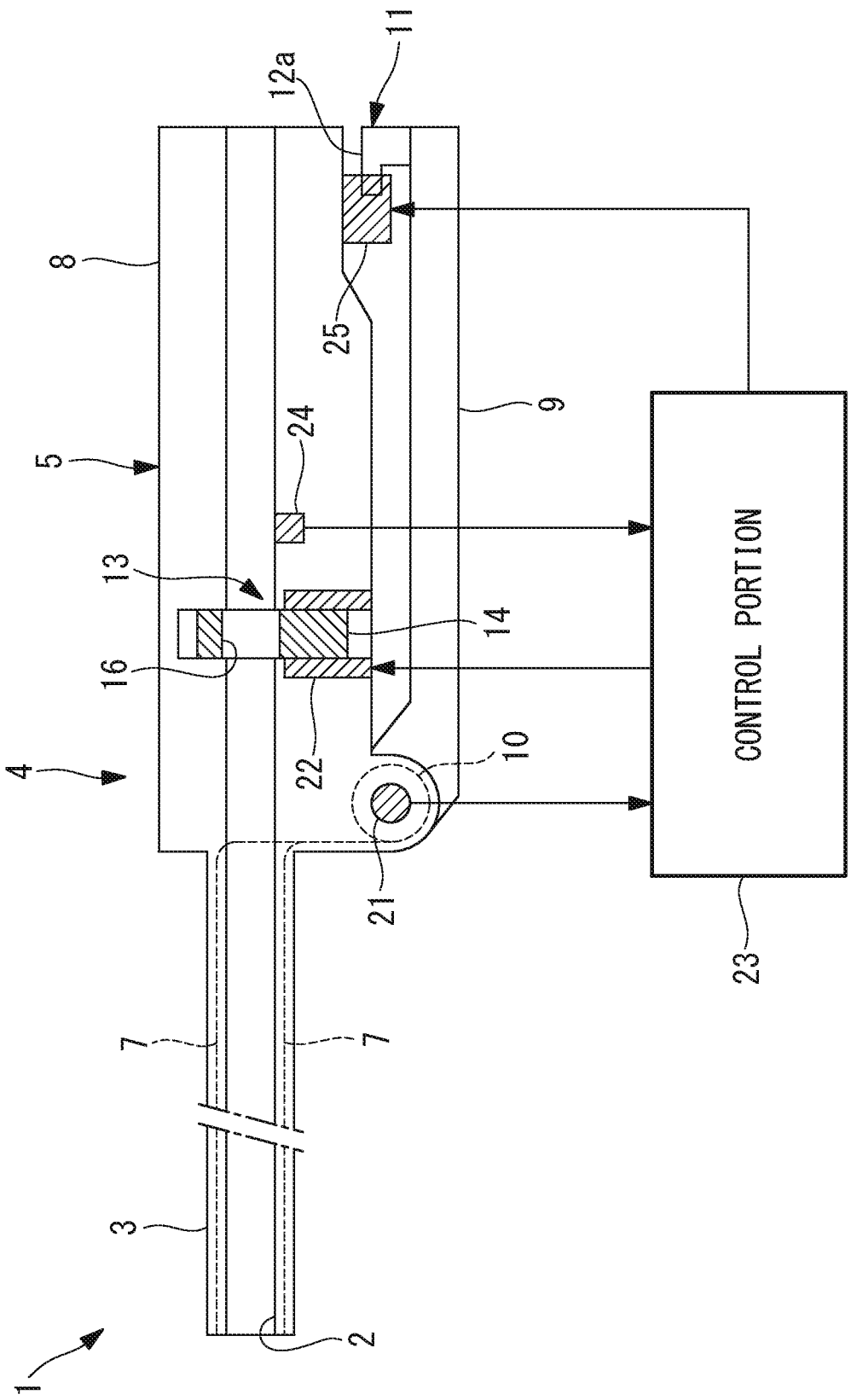

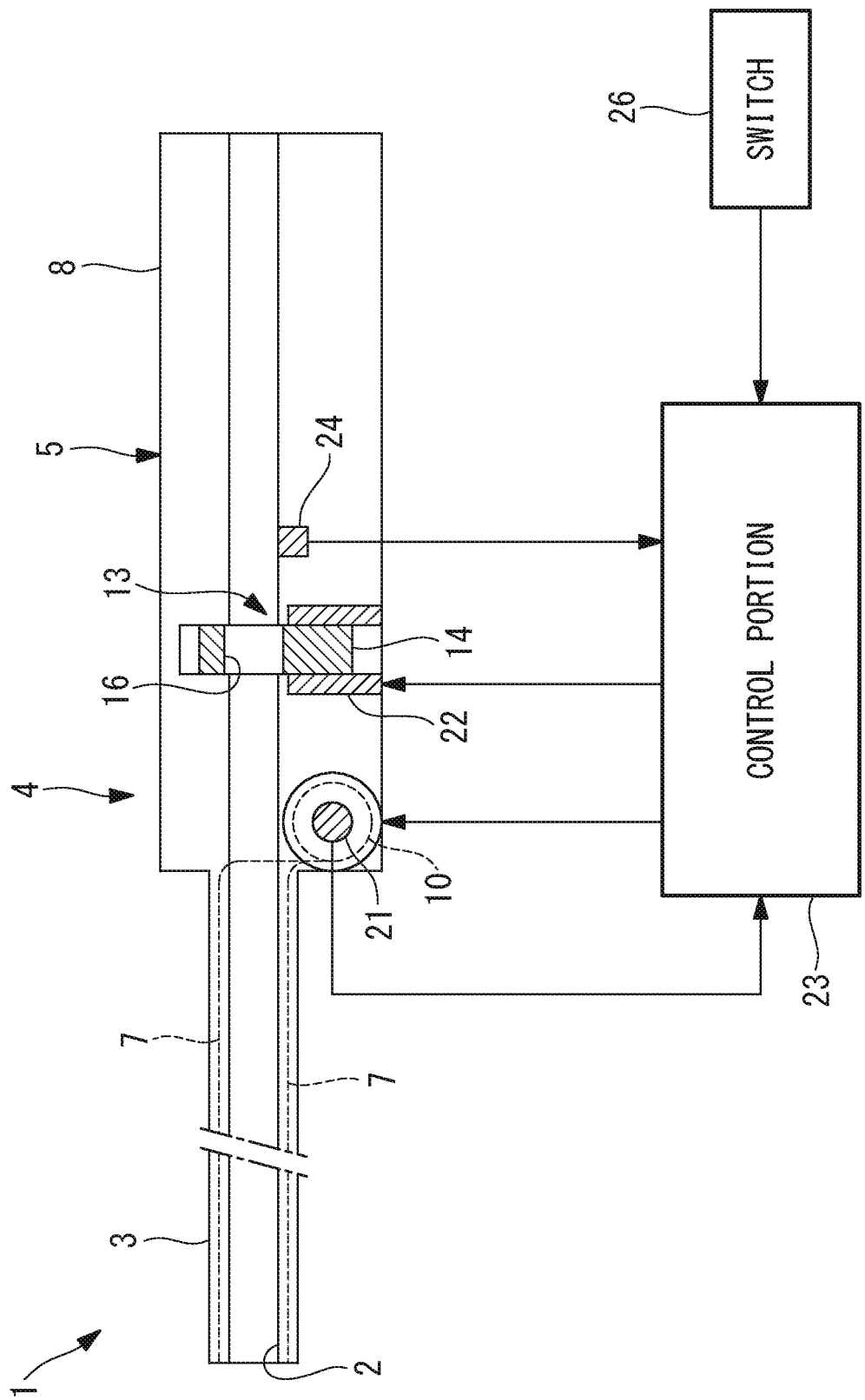

OVERTUBE AND MEDICAL SYSTEM

CROSS-REFERENCE TO RELATED APPLICATIONS

This is a continuation of International Application PCT/JP2017/013983, with an international filing date of Apr. 3, 2017, which is hereby incorporated by reference herein in its entirety.

TECHNICAL FIELD

The present invention relates to an overtube and a medical system.

BACKGROUND ART

There is a known overtube that is formed in a tube shape by arraying numerous nested annular members and that is capable of maintaining (shape locking) an arbitrary shape by means of frictional forces generated between the annular members as a result of the annular members being brought into firm contact with each other in a longitudinal-axis direction due to a pulling force of a wire (for example, see Japanese Unexamined Patent Application, Publication No. 2009-279412). Such an overtube is inserted into a body cavity in a state in which the shape lock is released and the shape thereof can be freely deformed, and, subsequently, as a result of shape locking by pulling the wire, it is possible to insert a medical device into a channel without exerting a load on tissue in the body cavity in the surrounding area.

SUMMARY OF INVENTION

An aspect of the present invention is a medical overtube including: a flexible elongated portion provided with a channel, the channel is configured to pass therethrough in a longitudinal direction of the elongated portion so as to insert a medical device; a shape fixing mechanism provided in the elongated portion, that the shape fixing mechanism is configured to switch the state of the elongated portion between a bendable state and a shaped-fixed state; and a gate mechanism disposed on a base-end side of the elongated portion, the gate mechanism is configured to close the channel when the state of the elongated portion is switched to the bendable state, and open the channel when the state of the elongated portion is switched to the shaped-fixed state.

Another aspect of the present invention is a medical system including: an elongated medical device; a flexible overtube provided with a channel, the channel is configured to pass therethrough in a longitudinal direction of the overtube so as to insert a medical device, and the overtube is configured to introduce the medical device into a body of a patient by inserting the medical device thereinto; a shape fixing mechanism configured to switch the state of the overtube between a bendable state and a shape-fixed state; and a gate mechanism configure to close the channel when the state of the overtube is switched to the bendable state and open the channel when the state of the overtube is switched to the shaped-fixed state.

BRIEF DESCRIPTION OF DRAWINGS

FIG. 8 is a longitudinal cross-sectional view showing a second modification of the overtube in FIG. 1.

FIG. 9 is a longitudinal cross-sectional view showing a third modification of the overtube in FIG. 1.

DESCRIPTION OF EMBODIMENT

An overtube 1 and a medical system 100 according to an embodiment of the present invention will be described below with reference to the drawings.

Figure 5:
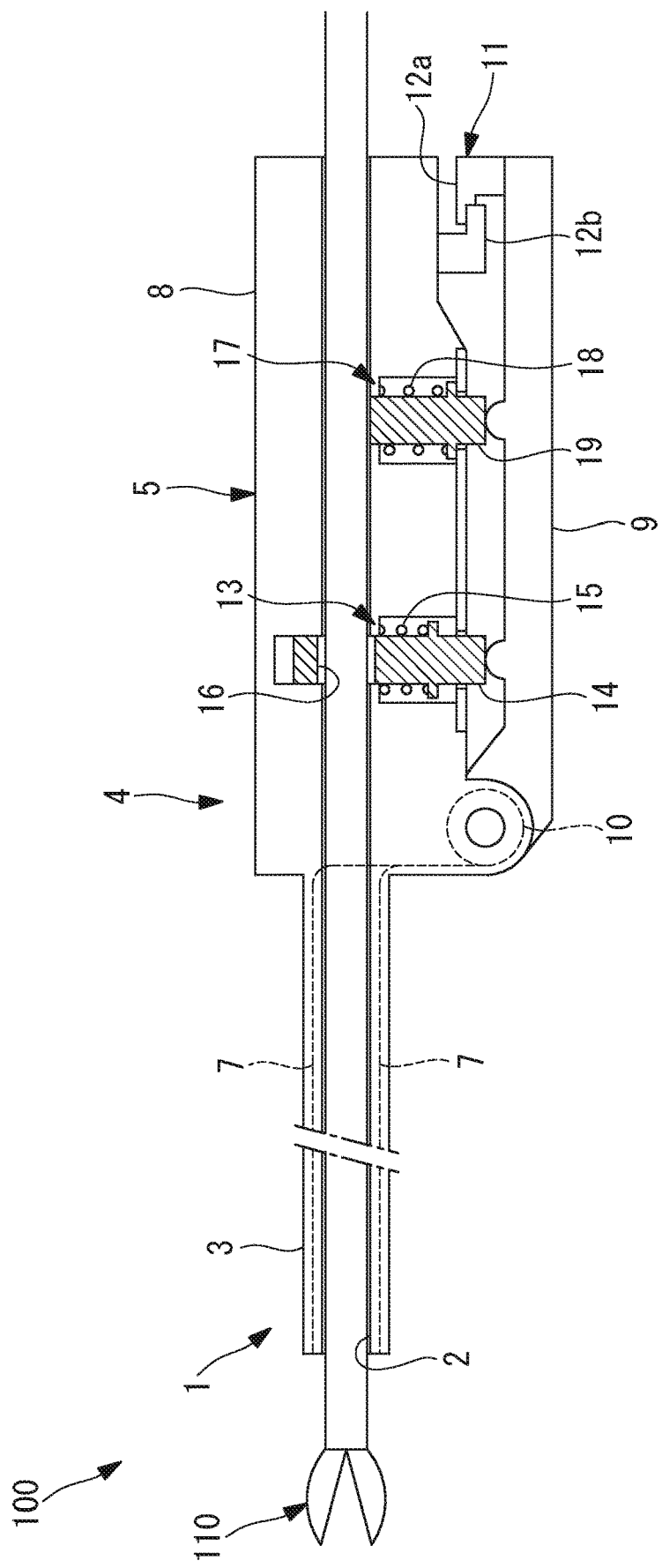
FIG. 5 is a longitudinal cross-sectional view showing a state in which a medical device is inserted into the overtube in FIG. 3.

As shown in FIG. 5, the medical system 100 according to this embodiment is provided with: a medical treatment tool (medical device) 110, such as gripping forceps, that treats a treatment target site; and the overtube 1.

Figure 1:
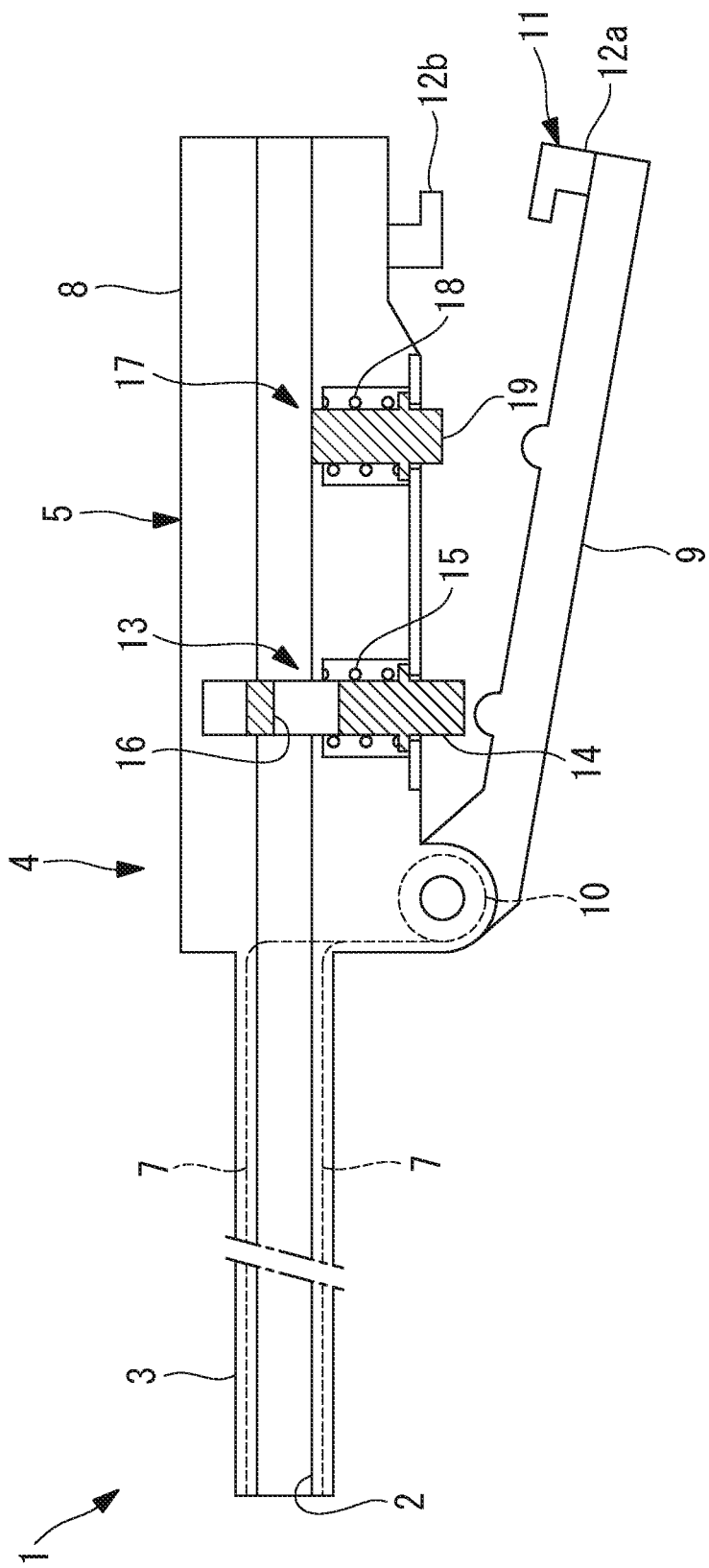
FIG. 1 is a longitudinal cross-sectional view showing an overtube according to an embodiment of the present invention.

As shown in FIG. 1, the overtube 1 according to this embodiment is provided with: an elongated tube main body (elongated portion) 3 having a channel 2 that passes therethrough in a longitudinal direction; and a shape fixing mechanism 4 that switches the state of the tube main body 3 between a shape-fixed state and a bendable state.

The tube main body 3 is formed, for example, as in the related art, in a tube-like shape by arraying numerous nested annular members (not shown). The channel 2 provided in the tube main body 3 is a through-hole having a circular cross-sectional shape and an inner diameter that is slightly greater than an outer diameter of the medical treatment tool 110 having a circular cross-sectional shape.

The shape fixing mechanism 4 is provided with: an operating portion 5 that is provided at a base end of the tube main body 3; and a wire 7 that brings the nested annular members into firm contact with each other by being pulled as a result of an operator operating the operating portion 5.

The operating portion 5 is provided with: a base member 8 that is secured to a base end of the tube main body 3; a lever (operating member) 9 that is attached to the base member 8 so as to be pivotable about an axis that is orthogonal to the longitudinal axis of the tube main body 3; and a pulley 10 that is secured to the lever 9 and that is rotated in association with pivoting of the lever 9. The wire 7 is wound around the pulley 10, so that pivoting of the lever 9 causes the pulley 10 to be rotated and the wire 7 is consequently pulled. Therefore, it is possible to fix the shape of the bent tube main body 3.

Figure 2A:
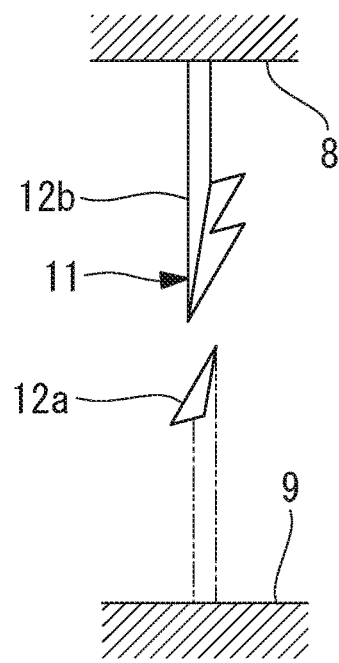
FIG. 2A is a diagram showing a state in which a ratchet mechanism provided in the overtube in FIG. 1 is released.
Figure 2B:
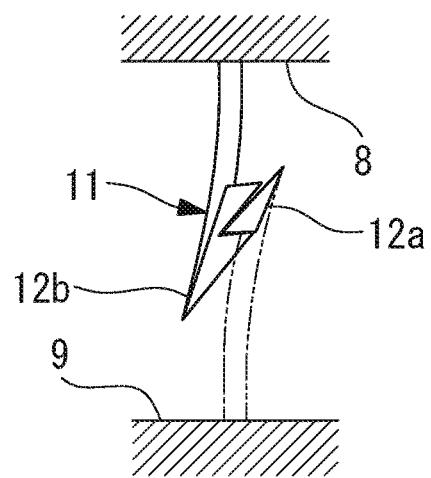
FIG. 2B is a state in which engagement pieces of the ratchet mechanism in FIG. 2A are engaged with each other.
Figure 2C:
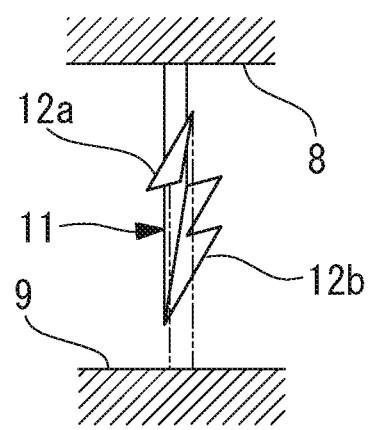
FIG. 2C is a diagram showing a state in which the engagement pieces of the ratchet mechanism in FIG. 2B are moved to positions at which the engagement between the engagement pieces with each other is released.
Figure 3:
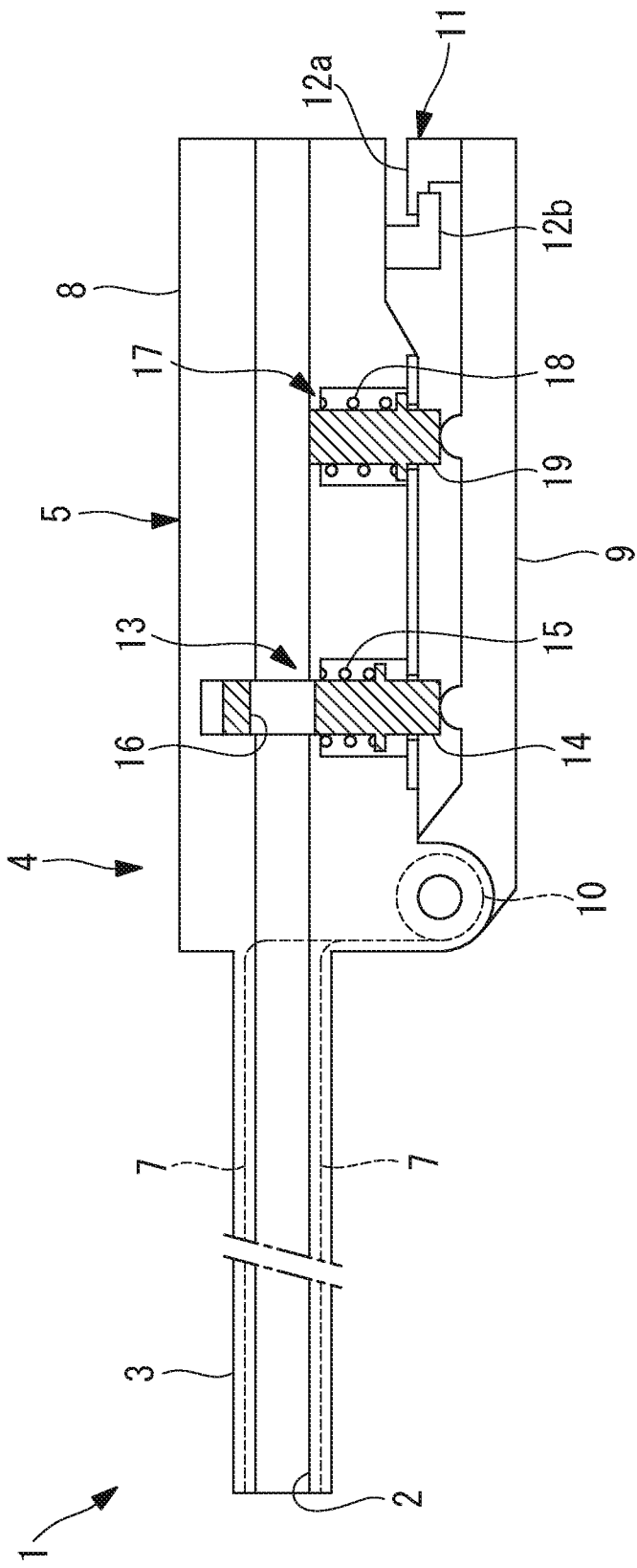
FIG. 3 is a longitudinal cross-sectional view showing the overtube in FIG. 1 in which the ratchet mechanism is placed in the state in FIG. 2B by pivoting a lever.
Figure 4:
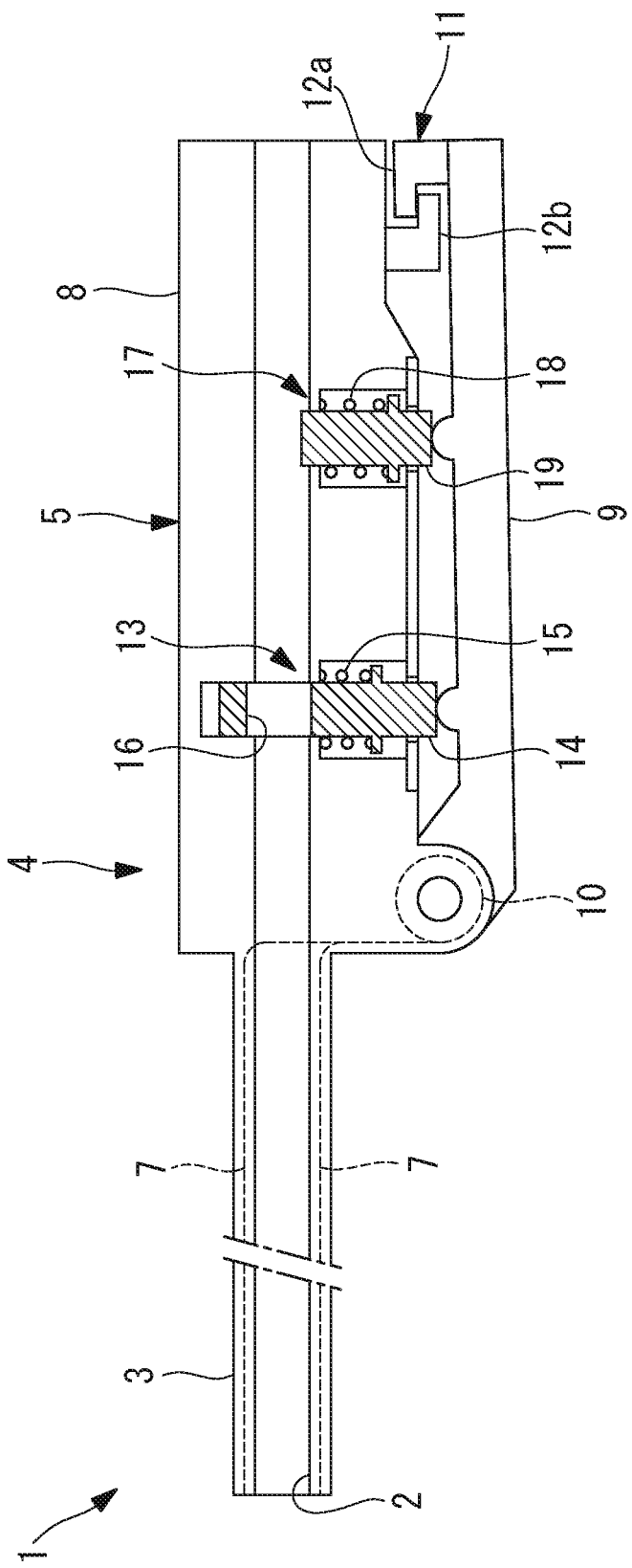
FIG. 4 is a longitudinal cross-sectional view showing the overtube in FIG. 1 in which the ratchet mechanism is placed in the state in FIG. 2C by pivoting the lever.

Between the lever 9 and the base member 8, a ratchet mechanism 11 shown in FIGS. 2A to 2C is provided. The ratchet mechanism 11 is provided with a pair of engagement pieces 12*a* and 12*b*, which are formed of plate springs individually attached to the lever 9 and the base member 8, and is configured so that it is possible to maintain the tube main body 3 at a position in which the shape thereof is fixed by achieving an engaged state in which the engagement pieces 12*a* and 12*b* are engaged with each other, as shown in FIGS. 2B and 3, as a result of the lever 9 being gripped. The ratchet mechanism 11 is configured so that the state in FIG. 2A is restored by releasing the engagement between the engagement pieces 12*a* and 12*b* with each other, as shown in FIGS. 2C and 4, as a result of even more firmly gripping the lever 9 from the engaged state, thus switching the state of the tube main body 3 to the bendable state by relaxing the wire 7.

The operating portion 5 is provided with a gate mechanism 13 that opens/closes the channel 2 of the tube main body 3 in accordance with the pivoting position of the lever 9.

The gate mechanism 13 is provided with: a gate member 14 that is provided in the base member 8 so as to be movable in a direction that is orthogonal to the longitudinal axis of the tube main body 3; and a biasing member 15, such as a coil spring or the like, that biases the gate member 14 in a direction in which the channel 2 of the tube main body 3 is closed.

The gate member 14 is a member that has, for example, a through-hole 16 that is equivalent to the channel 2 of the tube main body 3, and that has a shaft shape in which the cross-section thereof is circular or polygonal, and is configured so as to open the channel 2 by moving the through-hole 16 to a position at which the through-hole 16 is aligned with the channel 2 and to close the channel 2 by moving the through-hole 16 to a position at which the through-hole 16 is displaced with respect to the channel 2. In this embodiment, the gate member 14 is configured so that, by partially closing the channel 2 instead of completely closing off the channel 2, it is possible to block the medical treatment tool 110 from being inserted into the tube main body 3.

In the state in which the lever 9 is pivoted to an open position, as shown in FIG. 1, the gate member 14 is separated from the lever 9 and is moved in a direction in which the gate member 14 closes the channel 2 due to a biasing force of the biasing member 15. Also, when the lever 9 is gripped and pivoted to a closed position, as shown in FIG. 3, the lever 9 presses the gate member 14, so that the gate member 14 is moved in a direction in which the gate member 14 opens the channel 2 by resisting the biasing force of the biasing member 15.

The operating portion 5 is provided with a switching blocking portion 17 that blocks the lever 9 from opening in the state in which the medical treatment tool 110 is inserted into the channel 2.

The switching blocking portion 17 is provided with a stopper 19 that is biased by the biasing member 18, such as a coil spring or the like, at a position that is retracted radially outward from the channel 2. As shown in FIG. 4, the stopper 19 is provided so as to protrude into the channel 2 as a result of being pushed by the lever 9 when the lever 9 is firmly gripped in order to release the engaged state held by the ratchet mechanism 11.

Specifically, in the case in which the lever 9 is firmly gripped in the state in which the medical treatment tool 110 having a lateral cross-section that is substantially equivalent to the lateral cross-section of the channel 2 is inserted into the channel 2, as shown in FIG. 5, the stopper 19 abuts against the medical treatment tool 110 and is restricted from moving so as to protrude into the channel 2, thus blocking the releasing of the engaged state of the ratchet mechanism 11. On the other hand, in the state in which the medical treatment tool 110 is not inserted into the channel 2, as shown in FIG. 4, it is possible to make the stopper 19 protrude into the channel 2 by firmly gripping the lever 9, and thus, it is possible to release the engaged state of the ratchet mechanism 11.

The operations of the overtube 1 and the medical system 100 according to this embodiment, thus configured, will be described below.

In order to introduce the medical treatment tool 110 into a body cavity by using the overtube 1 according to this embodiment, the tube main body 3 is set to the bendable state by decreasing the pulling force of the wire 7 exerted via the pulley 10 by achieving a state in which the lever 9 is not gripped by releasing the locked state held by the ratchet mechanism 11, as shown in FIG. 1.

By introducing the tube main body 3 into the body cavity in this state, it is possible to dispose a distal end of the tube main body 3 in the vicinity of a treatment target site in the body cavity while bending the tube main body 3 in conformity to the shape of the winding body cavity.

With the tube main body 3 disposed in the body cavity in this way in the bendable state, the gate member 14 of the gate mechanism 13 is not being pressed by the lever 9, the gate member 14 is biased in one direction by the biasing member 15, and the through-hole 16 is disposed at a position that is displaced from the channel 2. By doing so, even if an attempt is made to insert the medical treatment tool 110 into the through-hole 16 from a base-end side, the medical treatment tool 110 is blocked by the gate member 14, thus preventing the insertion thereof into the tube main body 3.

Specifically, even if the operator mistakenly attempts to insert the medical treatment tool 110 without fixing the shape of the tube main body 3, because the medical treatment tool 110, having a high rigidity, is prevented from being inserted into the tube main body 3 in the bendable state, the tube main body 3 is prevented from being deformed by the medical treatment tool 110, and thus, there is an advantage in that it is possible to effectively prevent a load from being exerted on tissue in the body cavity in a surrounding area.

Also, as a result of the operator pivoting the lever 9 in a direction in which the lever 9 is brought close to the base member 8 of the operating portion 5 disposed outside to body, as shown in FIG. 3, in the state in which the distal end of the tube main body 3 is disposed in the vicinity of the treatment target site, the wire 7 is pulled by rotating the pulley 10, and the tube main body 3 is fixed in the winding shape.

At this time, as a result of the lever 9 pressing the gate member 14 of the gate mechanism 13, the gate member 14 is moved while resisting the biasing force of the biasing member 15, and the through-hole 16 is disposed at a position at which the through-hole 16 is aligned with the channel 2. By doing so, the channel 2 is opened, and thus, it becomes possible to insert the medical treatment tool 110 into the tube main body 3. Then, in this state, because the ratchet mechanism 11 provided between the lever 9 and the base member 8 immobilizes the lever 9 with respect to the base member 8, the state in which the insertion of the medical treatment tool 110 into the tube main body 3 is allowed is maintained.

As a result of the operator inserting the medical treatment tool 110 into the channel 2 of the tube main body 3 in this state, as shown in FIG. 5, it is possible to treat the treatment target site by using the medical treatment tool 110 by causing the medical treatment tool 110 to protrude from the distal end of the tube main body 3 disposed in the vicinity of the treatment target site.

In this case, because the shape of the tube main body 3 is fixed by the operation of the shape fixing mechanism 4, even if the medical treatment tool 110 having a high rigidity is inserted into the channel 2, the tube main body 3 is prevented from being deformed, and thus, it is possible to prevent a burden from being exerted on the body cavity in the surrounding area.

With the overtube 1 according to this embodiment, because the stopper 19 provided in the base member 8 comes into contact with both the lever 9 and the medical treatment tool 110 in the state in which the medical treatment tool 110 is inserted into the channel 2 of the shape-fixed tube main body 3 by pivoting the lever 9 in the direction in which the lever 9 is brought close to the base member 8, the motion in which the lever 9 is firmly gripped to pivot the lever 9 so as to bring the lever 9 even closer to the base member 8 is restricted. By doing so, the locked state held by the ratchet mechanism 11 is prevented from being released.

Specifically, because it is prohibited to release the shape fixing by the shape fixing mechanism 4 in the state in which the medical treatment tool 110 is inserted into the channel 2 of the shape-fixed tube main body 3, there is an advantage in that the state of the tube main body 3 would not be switched to the bendable state even if the operator mistakenly performs the operation to release the shape fixing. When the state of the tube main body 3 is switched to the bendable state in the state in which the medical treatment tool 110 remains inserted into the channel 2 of the shape-fixed tube main body 3, the medical treatment tool 110 having a high rigidity causes the tube main body 3 to be deformed, and a load is exerted on tissue in the body cavity in the surrounding area; however, with this embodiment, such a problem does not occur.

Also, because the stopper 19 is released after the medical treatment tool 110 is pulled out from the channel 2 of the shape-fixed tube main body 3, it is possible to release the locked state held by the ratchet mechanism 11 by firmly gripping the lever 9 with respect to the base member 8, as shown in FIG. 4. By doing so, it is possible to smoothly pull out the tube main body 3 from the body cavity as a result of switching the state of the tube main body 3 to the bendable state by decreasing the pulling force of the wire 7.

Figure 6:
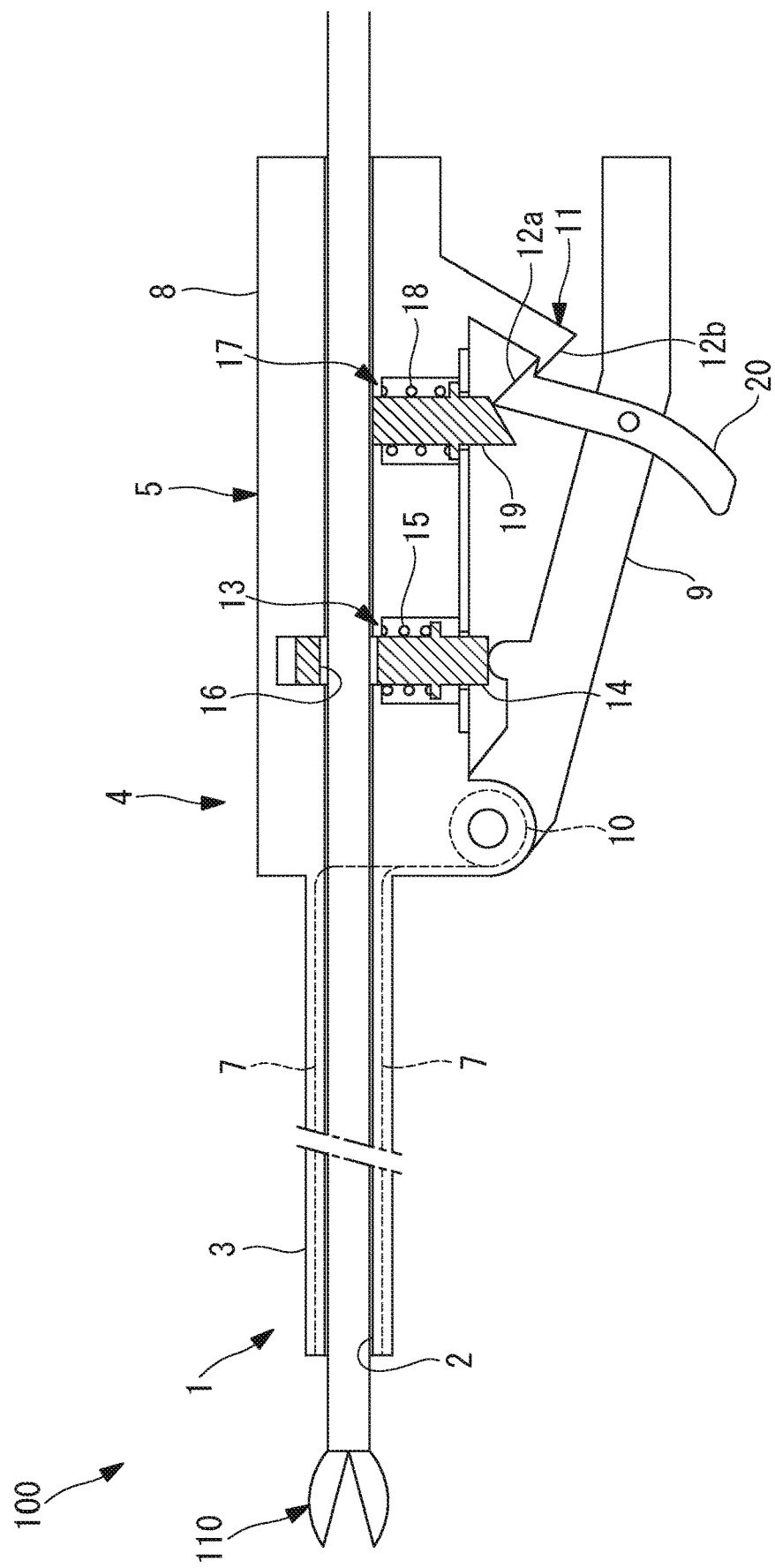
FIG. 6 is a longitudinal cross-sectional view showing a first modification of the overtube in FIG. 1 in a state in which a tube main body is locked in a shape-fixed state.
Figure 7:
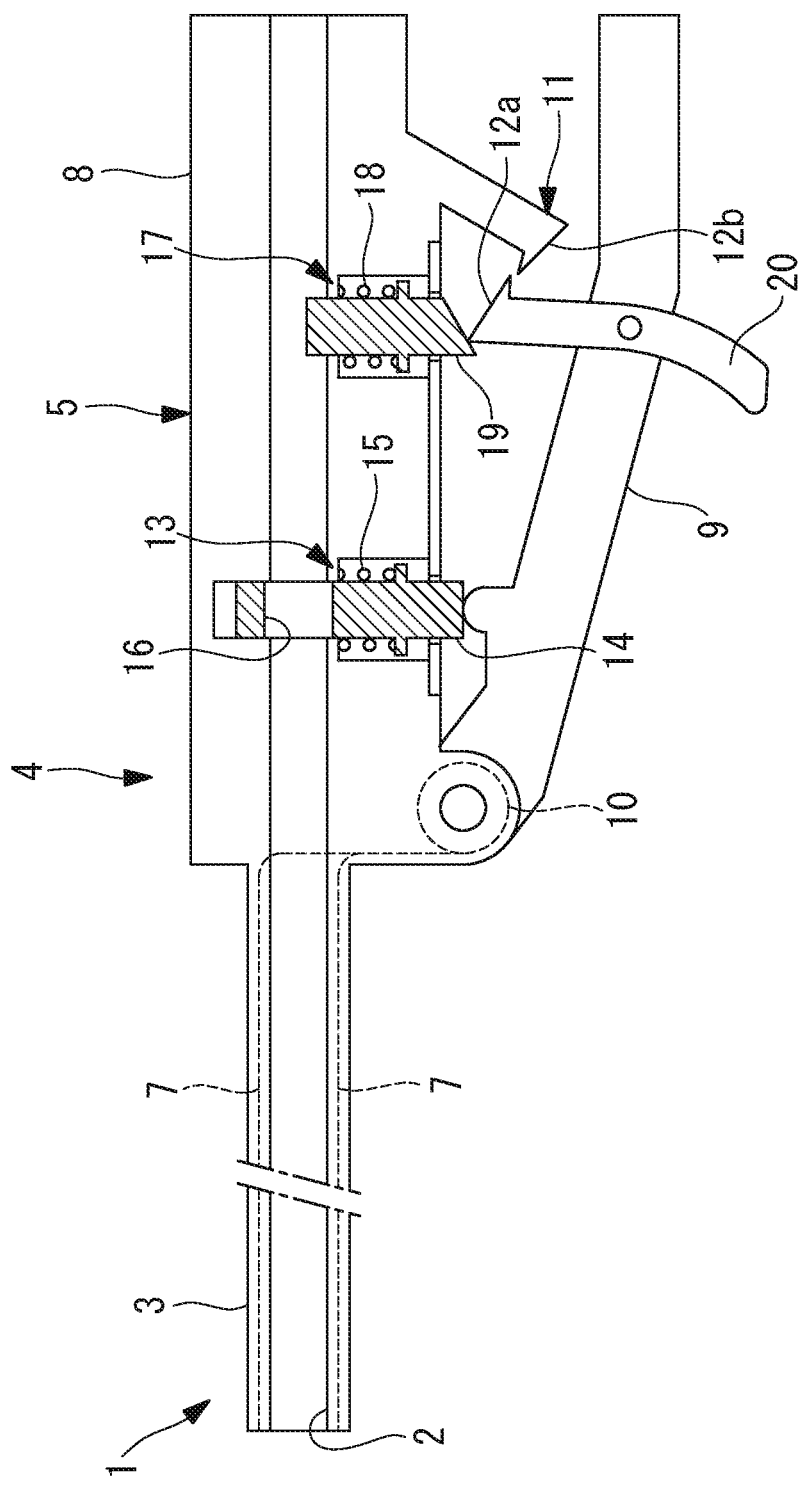
FIG. 7 is a longitudinal cross-sectional view showing a state in which the shape-fixing lock of the tube main body of the overtube in FIG. 6 can be released.

In the overtube 1 according to this embodiment, the operation of the lever 9 in which the locked state is released by firmly gripping the lever 9 is restricted by means of the stopper 19 sandwiched between the lever 9 and the medical treatment tool 110. Alternatively, as the ratchet mechanism 11, as shown in FIGS. 6 and 7, a mechanism having a structure in which a locked state is released by pivoting a releasing lever 20 may be employed, and the operation of the releasing lever 20 may be restricted by the stopper 19.

Although the shape fixing of the tube main body 3 and the opening of the channel 2 are linked by mechanically pressing the gate member 14, which is biased by the biasing member 15 in the direction in which the gate member 14 closes the channel 2, by means of the lever 9, alternatively, in this embodiment, the shape fixing of the tube main body 3 and the opening of the channel 2 may electrically be linked by detecting the angle of the lever 9 by means of an angle sensor (state sensor) 21 and by using a solenoid (gate driving portion) 22 that moves the gate member 14 on the basis of the detection results of the angle sensor 21, as shown in FIG. 8.

In FIG. 8, reference sign 23 is a control portion that changes a signal to be output to the solenoid 22 in accordance with the angle of the lever 9 detected by the angle sensor 21.

Although releasing of the shape fixing of the tube main body 3 in the state in which the medical treatment tool 110 is inserted in the channel 2 is blocked by mechanically pressing, by means of the lever 9, the stopper 19 that is biased by the biasing member 15 so as not to protrude into the channel 2, alternatively, in this embodiment, the presence/absence of the medical treatment tool 110 in the channel 2 may be detected by a sensor (device sensor) 24, and the locked state held by the ratchet mechanism 11 may be controlled by a solenoid (locking mechanism, switching blocking portion) 25 on the basis of the detection result of the sensor 24, as shown in FIG. 8.

Specifically, in the case in which the sensor 24 detects that the medical treatment tool 110 is not inserted into the channel 2, the control portion 23 is allowed to freely switch between the locked state and the lock-released state of the ratchet mechanism 11 in accordance of pivoting of the lever 9. On the other hand, in the case in which the sensor 24 detects that the medical treatment tool 110 is inserted into the channel 2, the control portion 23 prohibits switching to the lock-released state by means of the lever 9. By doing so, it is possible to prevent a load from being exerted on tissue in the body cavity as a result of the tube main body 3 being deformed in the body cavity.

Although the shape fixing mechanism 4 is operated by operating a lever, alternatively, as shown in FIG. 9, a motor-driven system may be employed in the pulley 10, and the switching between the shape-fixed state and bendable state of the tube main body 3 may be performed by means of a switch 26. In this case, the angle sensor 21 may detect the rotational angle of the pulley 10.

Specifically, upon the operator fixing the shape of the tube main body 3 by operating the switch 26, in the case in which the angle of the pulley 10 detected by the angle sensor 21 reaches a predetermined angle range, the control portion 23 causes the gate member 14 to be moved by operating the solenoid 22, and thus, it becomes possible to insert the medical treatment tool 110 into the channel 2. On the other hand, when the operator switches the state of the tube main body 3 to the bendable state by operating the switch 26 in the state in which the sensor 24 has detected that the medical treatment tool 110 is not inserted into the channel 2, the pulley 10 is rotated to relax the pulling force of the wire 7, and the gate member 14 is moved as a result of the control portion 23 activating the solenoid 22, and thus, the insertion of the medical treatment tool 110 into the channel 2 is blocked.

Even if the operator operates the switch 26 and switches the state of the tube main body 3 to the bendable state in the state in which the sensor 24 has detected that the medical treatment tool 110 is inserted into the channel 2, the control portion 23 does not allow the pulley 10 to be rotated, and thus, the tube main body 3 is maintained in the shape-fixed state. By doing so, it is possible to block the state of the tube main body 3 from being switched to the bendable state in the state in which the medical treatment tool 110 is inserted into the channel 2. In this case, the control portion 23 and the motor that drives the pulley 10 serve as switching blocking portions.

As a result, the following aspect is read from the above described embodiment of the present invention.

An aspect of the present invention is an overtube including: a flexible elongated portion that is provided with a channel that passes therethrough in a longitudinal direction; a shape fixing mechanism that is capable of switching the state of the elongated portion between a bendable state and a shape-fixed state; and a gate mechanism that is disposed on a base-end side of the elongated portion, that closes the channel when the state of the elongated portion is switched to the bendable state by the shape fixing mechanism, and that opens the channel when the state of the elongated portion is switched to the shape-fixed state by the shape fixing mechanism.

With this aspect, as a result of inserting the elongated portion into the body cavity after switching the state thereof to the bendable state by means of the shape fixing mechanism, it is possible to smoothly insert the elongated portion by bending the elongated portion in conformity to the shape of the winding body cavity. In the state in which a distal end of the elongated portion is disposed in the vicinity of a treatment target site in the body cavity, the shape of the elongated portion is fixed by operating the shape fixing mechanism.

Because the gate mechanism is operated once the shape of the elongated portion is fixed and the channel in the elongated portion is opened, by inserting the medical device into the channel from a base-end side of the channel in this state, it is possible to make a distal end of a medical device reach the treatment target site. Because the shape of the elongated portion is fixed, the shape of the elongated portion does not change even if a medical device having a high rigidity is inserted into the channel, and thus, it is possible to prevent a load from being exerted on tissue in the body cavity in the surrounding area.

Because the channel is closed by the gate mechanism in the state in which the shape of the elongated portion is not fixed by the shape fixing mechanism, the insertion of the medical device into the channel is prohibited. By doing so, the shape of the elongated portion is prevented from being deformed as a result of a medical device having a high rigidity being inserted into the channel of the elongated portion in the state in which the shape thereof is not fixed, and thus, it is possible to prevent a load from being exerted on tissue in the body cavity in the surrounding area.

The above-described aspect may be provided with a switching blocking portion that blocks the switching of the state of the elongated portion to the bendable state by the shape fixing mechanism in the state in which the medical device is inserted into the channel By doing so, in the state in which treatment is being performed by inserting a medical device into the channel of the shape-fixed elongated portion, the switching blocking portion blocks switching of the state of the elongated portion to the bendable state, and thus, it is possible to prevent the elongated portion from being deformed by the rigidity of the medical device.

In the above-described aspect, the shape fixing mechanism may additionally be provided with an operating member that switches the state of the elongated portion between the bendable state and the shape-fixed state by being moved via the operation thereof by an operator, and the switching blocking portion may be a stopper that abuts against the medical device inserted into the channel and the operating member and that prohibits the movement of the operating member to the position for the bendable state from the position for the shape-fixed state.

By doing so, when an operator operates the operating member, the state of the elongated member is switched between the bendable state and the shape-fixed state due to the movement of the operating member. In the state in which the medical device is inserted into the channel of the elongated portion, the stopper abuts against the medical device and the operating member. By doing so, the operating member is prohibited to move from the position for the shape-fixed state to that for the bendable state.

The above-described aspect may be provided with a state sensor that detects the state of the elongated portion that is switched by the shape fixing mechanism, and the gate mechanism may be provided with a gate driving portion that opens/closes the channel on the basis of the state of the elongated portion detected by the state sensor.

By doing so, the gate driving portion opens the channel in the case in which the state sensor detects that the elongated portion is in the shape-fixed state, and the gate driving portion closes the channel in the case in which the state sensor detects that the elongated portion is in the bendable state.

The above-described aspect may be provided with a device sensor that detects whether or not the medical device is inserted into the channel, and a switching blocking portion that blocks the switching of the state of the elongated portion to the bendable state by the shape fixing mechanism in the state in which the device sensor has detected the insertion of the medical device.

By doing so, the switching blocking portion blocks the switching of the state of the elongated portion to the bendable state in the case in which the device sensor detects that the medical device is inserted into the channel. By doing so, in the state in which treatment is being performed by inserting a medical device into the channel of the shape-fixed elongated portion, the switching blocking portion blocks switching of the state of the elongated portion to the bendable state, and thus, it is possible to prevent the elongated portion from being deformed by the rigidity of the medical device.

In the above-described aspect, the shape fixing mechanism may additionally be provided with an operating member that switches the state of the elongated portion between the bendable state and the shape-fixed state by being moved via the operation thereof by an operator, and, the switching blocking portion may be a locking mechanism that immobilizes the operating member in the state in which the device sensor has detected the insertion of the medical device.

By doing so, when an operator operates the operating member, the state of the elongated member is switched between the bendable state and the shape-fixed state due to the movement of the operating member. In the state in which the medical device is inserted into the channel of the elongated portion, the operating member is immobilized by the locking mechanism, and thus, it is possible to prevent the state of the elongated portion from being switched to the bendable state from the shape-fixed state.

Another aspect of the present invention is a medical system provided with any one of the above-described overtubes and a medical device that is inserted via the channel of the overtube.

REFERENCE SIGNS LIST 1 overtube
2 channel
3 tube main body (elongated portion)
4 shape fixing mechanism 9 lever (operating member)
13 gate mechanism
17 switching blocking portion
19 stopper (switching blocking portion)
21 angle sensor (state sensor)
22 solenoid (gate driving portion)
24 sensor (device sensor)
25 solenoid (locking mechanism, switching blocking portion)
100 medical system
110 medical treatment tool (medical device)

The invention claimed is:

1. A medical overtube comprising:
an operating portion;
a flexible elongated tube having a proximal end connected to the operating portion, the operating portion and the tube being provided with a channel configured to receive a medical device, the channel extending longitudinally from a proximal opening in the operating portion to a distal opening in the tube, the tube being configured to switch between a bendable state and a shape-fixed state; and
an obstruction movably disposed in the operating portion, the obstruction being configured to:
have a first position at least partially obstructing a first portion of the channel corresponding to the operating portion to prevent insertion of the medical device into a second portion of the channel corresponding to the tube when the tube is in the bendable state; and
have a second position allowing the medical device to enter the second portion of the channel from the first portion of the channel when the tube is in the shape-fixed state.

2. The medical overtube according to claim 1, further comprising a stopper disposed in the operating portion, the stopper being configured to restrict switching the tube from the shape-fixed state to the bendable state when the medical device is inserted into the channel.

3. The medical overtube according to claim 2, further comprising:
a shape fixing mechanism configured to switch the tube between the shape-fixed state and the bendable state, the shape-fixing mechanism comprising a lever configured to switch the tube between a third position corresponding to the bendable state and a fourth position corresponding to the shape-fixed state,
wherein the stopper is configured to restrict movement of the lever so as to block the switching from the shape-fixed state to the bendable state when the medical device is inserted into the channel.

4. The medical overtube according to claim 1, further comprising:
a first sensor configured to detect whether the tube is in the bendable state or in the shape-fixed state, and
an actuator configured to move the obstruction to the first position when the first sensor detects the tube being in the bendable state and move the obstruction to the second position when the first sensor detects the tube being in the shape-fixed state.

5. The medical overtube according to claim 1, further comprising:
a first sensor configured to detect whether the medical device is inserted into the channel; and
a locking mechanism configured to restrict the tube from switching from the shape-fixed state to the bendable state when the first sensor detects that the medical device is inserted into the channel.

6. The medical overtube according to claim 5, further comprising:
a shape fixing mechanism configured to switch the tube between the shape-fixed state and the bendable state, the shape-fixing mechanism comprising a lever configured to switch the tube between a third position corresponding to the bendable state and a fourth position corresponding to the shape-fixed state,
wherein the locking mechanism is configured to restrict movement of the lever when the first sensor detects that the medical device is inserted into the channel.

7. The medical overtube according to claim 1, further comprising a shape fixing mechanism configured to switch the tube between the shape-fixed state and the bendable state.

8. The medical overtube according to claim 1, further comprising:
a rotatable pulley; and
a wire disposed in the tube and having an end connected to the pulley such that rotating the pulley in a first direction switches the tube to the bendable state and rotating the pulley in a second direction, opposite to the first direction, switches the tube to the shape-fixed state.

9. The medical overtube according to claim 8, further comprising:
a lever operatively connected to the pulley, the lever being configured to rotate between a third position corresponding to the pulley being rotated in the first direction and a fourth position corresponding to the pulley being rotated in the second direction;
a ratchet configured to lock the lever to the operating portion when the lever is rotated into the fourth position.

10. The medical overtube according to claim 1, wherein the obstruction is movable in a direction perpendicular to a longitudinal direction of the first portion of the channel between the first position at least partially obstructing the first portion of the channel and the second position allowing the medical device to enter the second portion of the channel from the first portion of the channel.

11. The medical overtube according to claim 10, wherein the obstruction includes a hole, the hole being aligned with the channel in the first position and the hole being offset from the channel in the second position.

12. A medical system comprising:
an elongated medical device; and
a medical overtube configured to introduce the medical device into a body of a patient by inserting the medical device into the medical overtube, the medical overtube comprising:
an operating portion;
a flexible elongated tube having a proximal end connected to the operating portion, the operating portion and the tube being provided with a channel configured to receive the medical device, the channel extending longitudinally from a proximal opening in the operating portion to a distal opening in the tube, the tube being configured to switch between a bendable state and a shape-fixed state; and
an obstruction movably disposed in the operating portion, the obstruction being configured to:
have first position at least partially obstructing a first portion of the channel corresponding to the operating portion to prevent insertion of the medical device into a second portion of the channel corresponding to the tube when the tube is in the bendable state; and have a second position allowing the medical device to enter the second portion of the channel from the first portion of the channel when the tube is in the shape-fixed state.

13. The medical system according to claim 12, further comprising a stopper disposed in the operating portion, the stopper being configured to restrict switching the tube from the shape-fixed state to the bendable state when the medical device is inserted into the channel.

14. The medical system according to claim 12, further comprising:

a first sensor configured to detect whether the tube is in the bendable state or in the shape-fixed state; and an actuator configured to move the obstruction to the first position when the first sensor detects the tube being in the bendable state and move the obstruction to the second position when the first sensor detects the tube being in the shape-fixed state.

15. The medical system according to claim 12, further comprising:

a first sensor configured to detect whether the medical device is inserted into the channel; and a locking mechanism configured to restrict the tube from switching from the shape-fixed state to the bendable state when the first sensor detects that the medical device is inserted into the channel.

16. The medical system according to claim 12, wherein the medical overtube further comprising a shape fixing mechanism configured to switch the tube between the shape-fixed state and the bendable state.

17. The medical system according to claim 12, further comprising:

a rotatable pulley; and a wire disposed in the tube and having an end connected to the pulley such that rotating the pulley in a first direction switches the tube to the bendable state and rotating the pulley in a second direction, opposite to the first direction, switches the tube to the shape-fixed state.

18. The medical system according to claim 17, further comprising:

a lever operatively connected to the pulley, the lever being configured to rotate between a third position corresponding to the pulley being rotated in the first direction and a fourth position corresponding to the pulley being rotated in the second direction;

a ratchet configured to lock the lever to the operating portion when the lever is rotated into the fourth position.

19. The medical system according to claim 12, wherein the obstruction is movable in a direction perpendicular to a longitudinal direction of the first portion of the channel between the first position at least partially obstructing the first portion of the channel and the second position allowing the medical device to enter the second portion of the channel from the first portion of the channel.

20. The medical system according to claim 19, wherein the obstruction includes a hole, the hole being aligned with the channel in the first position and the hole being offset from the channel in the second position.

* * * * *